United States Patent [19]

Schwarzmann

[11] 4,243,883
[45] Jan. 6, 1981

[54] BLOOD HEMATOCRIT MONITORING SYSTEM

[75] Inventor: Frank Schwarzmann, Colgate, Wis.

[73] Assignee: Midwest Cardiovascular Institute Foundation, Wauwatosa, Wis.

[21] Appl. No.: 4,758

[22] Filed: Jan. 19, 1979

[51] Int. Cl.³ .................... G01J 1/00; G01N 33/48
[52] U.S. Cl. .................................. 250/343; 356/40
[58] Field of Search ........................... 356/40, 39, 41;
250/343; 128/633, 214 R, 214 E; 23/913;
422/44, 45

[56] References Cited

U.S. PATENT DOCUMENTS

| | | | |
|---|---|---|---|
| 2,836,096 | 5/1958 | Korman | 356/40 |
| 3,029,682 | 4/1962 | Wood | 356/41 |
| 3,183,908 | 5/1965 | Collins et al. | 422/45 |
| 3,427,135 | 2/1969 | Pelavin et al. | 23/230 B |
| 3,802,776 | 4/1974 | Tchang | 356/41 |
| 3,989,625 | 11/1976 | Mason | 128/214 E |
| 4,067,320 | 1/1978 | Olsson et al. | 250/343 |

Primary Examiner—Eli Lieberman
Assistant Examiner—Carolyn E. Fields
Attorney, Agent, or Firm—John C. Cooper, III

[57] ABSTRACT

A system for continuously monitoring and/or controlling blood hematocrit levels is disclosed. The system includes a photometric hematocrit sensor which is coupled to a linear response meter, and in one embodiment a separate sensor is coupled to a three-way solenoid valve. The sensor is responsive to the hemoglobin density in the optical path. The valve system automatically causes diversion of solution having a degree of hematocrit dilution below a set minimum. The sensor is independent of the amount of oxy-hemoglobin (HbO$_2$) and reduced hemoglobin (HHb) and the system allows for instantaneous detection of improper hematocrit levels and obviates the need for time-consuming and unreliable centrifugal micro-hematocrit tests.

11 Claims, 5 Drawing Figures

BLOOD HEMATOCRIT MONITORING SYSTEM

FIELD OF THE INVENTION

The present invention relates generally to the art of monitor and control systems, and in particular to monitor and control systems useful to monitor hematocrit levels and control them at or above a prescribed minimum.

BACKGROUND OF THE INVENTION

It is common in cardiovascular surgery to add various solutions to the blood stream. For example, during cardio-pulmonary bypass surgery, the procedures require proportionally large quantities of solutions for blood volume support, pump oxygenator prime and myocardial protection. The solutions may include whole blood, plasma, salt solutions, nutrient solutions and the like.

During the course of such an operation, a careful watch must be maintained on the level of hematocrit in the blood flowing through the body. Typically this is done by taking samples at intervals and determining hematocrit levels by well known methods, including centifugal micro-hematocrit tests. Because such tests are conducted at intervals they are not able to detect sudden changes in hematocrit levels. Moreover, such tests are not always reliable and are always susceptible to technician error. If hematocrit levels are not maintained at or above certain levels, irreparable damage may occur to the patient in a relatively short period of time.

In addition to the example provided above for cardiovascular bypass surgery, there are other medical procedures where constant monitoring and control of certain fluid constituents is important.

While numerous methods are known for precisely determining hematocrit levels and the levels of other fluid constituents, the present inventor is unaware of any system which incorporates the measurement, monitor and control functions which would be necessary for the use of such system during operations.

A reliable system for monitoring and controlling the level of fluid constituents for such purposes would be a significant advance in the art.

OBJECTS OF THE INVENTION

It is a primary object of the present invention to provide a system for monitoring a fluid flow to continuously measure the level of a particular blood constituent thereof.

It is another object of the present invention to provide a novel system for monitoring, and in some cases controlling, hematocrit levels in a blood solution.

Another object of the present invention is to provide such a monitor system which may be used during an operative procedure.

Still another object of the present invention is to provide such a monitor system which operates continuously and which provides rapid responses to preset fluid conditions.

Yet another object of the present invention is to provide a monitor system which includes an electrical circuit which provides a linearized response to the constituent level.

How these and other objects of the invention are accomplished will be described in the following specification taken in conjunction with the figures. Generally, however, the objects are accomplished in one embodiment of the invention by a monitor and control system which includes two sensors, two meters and a three-way solenoid valve. By way of example, the invention can briefly be described with reference to the embodiment useful for monitoring and controlling blood hematocrit levels during pulmonary by-pass surgery. A first blood flow loop includes the patient's body, a blood oxygenator pump system and one sensor and meter system. It is also assumed that various flow lines are coupled to the body for supplying certain fluids to the blood stream. Another loop includes the blood suction return line and the oxygenator pump. A photometric sensor and meter are also provided on this loop for continuously measuring the hematocrit level of the blood flowing therethrough. The sensors include a light source and a photoreceptor designed for generating an electric voltage in response to the light impinging thereon. The response is sent to a meter which provides a visual indication of the hematocrit level. In the suction return loop the meter is coupled to the solenoid valve to prevent blood from being added to the primary loop in the event the hematocrit level in the blood suction line falls below a preselected minimum.

DESCRIPTION OF THE PREFERRED EMBODIMENT

Figure 1:
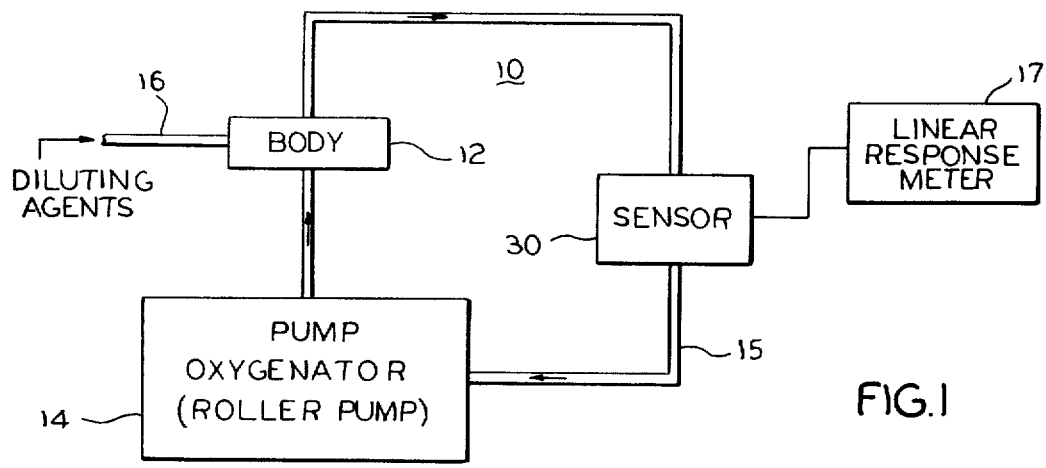
FIG. 1 is a schematic diagram of a hematocrit monitor system of the present invention useful during cardio-pulmonary by-pass surgery.

Referring now to FIG. 1, a hematocrit monitor system 10 of the present invention is shown in schematic form for use during by-pass surgery, e.g. the type of surgery used for heart valve work or repair of coronary blood vessels. In such surgery, blood from the body 12 bypasses the heart and is passed through a pump oxygenator unit 14, the latter being known to the art and in and of itself forming no part of the present invention. However, for purposes of explanation, the unit removes undesirable components from the blood and converts reduced hemoglobin (HHb) to oxygenated hemoglobin ($HbO_2$). The pump 14 forces the blood through the body and, during the operation, serves the purpose of the heart muscle. In FIG. 1 it can also be noted that a diluting agent inlet line 16 is shown entering the body, through which various diluting agents are added to the body. Numerous of such lines may actually be used during this type of surgery. Examples of typical diluting agents which may be used during such operations include whole blood, plasma, salt solutions, nutrient fluids and the like. The solutions are necessary for life support, pump prime and to make up blood volumes which might be diminished during surgery. Unless careful control of the addition of diluting agents is exercised, however, the blood hematocrit level can be reduced to critically low levels. In the present invention, the monitor system is adapted for visually displaying the hematocrit level to the surgeon or his assistants.

To this end an optically transparent lumen 22 (see FIG. 2) is inserted in the main flow loop 15, the lumen being disposed between an infra-red light source 24 and a photo transistor detector 26. The detector 26 is selected from those which produce a change in voltage depending on the amount of light striking the detector surface and the components are selected so that the amount of such light is directly related to the hemoglobin density in the optical path. A visual picture of the level of hematocrit is provided by the linear response meter 17, details of which will be provided below.

The lumen 22, light source 24 and photo-detector 26 are located inside a sensor housing 30 which is interiorly coated with nonreflective material 32. Housing 30 is generally rectangular and preferably includes a removable cover and snug fitting lumen channel 35 to prevent extraneous light from entering the area of box 30 which houses the light source 24 and sensor 26.

Figure 2:
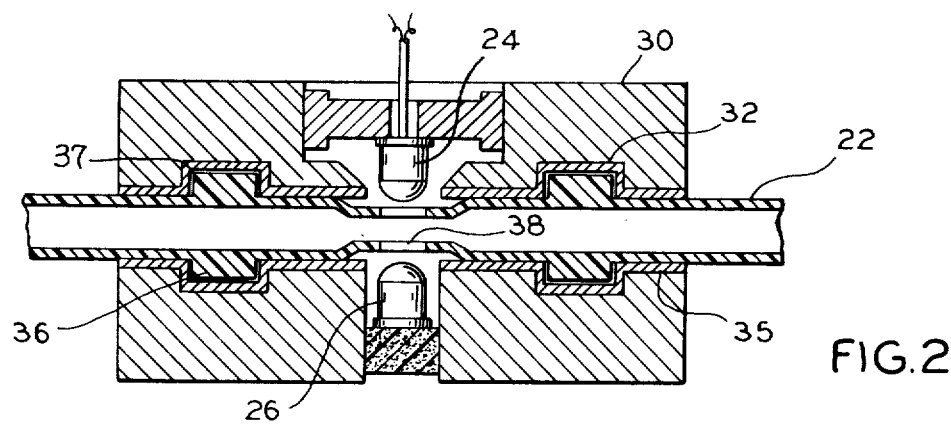
FIG. 2 is a top view of a photosensor device useful in the system shown in FIG. 1.

It can also be noted in FIG. 2 that the lumen 22 is generally circular in cross-section at the entrance and the exit of housing 30, but is generally square in cross-section in the middle between the light source and detector. Such an arrangement permits the light emitted from source 24 to pass directly through lumen 22 and, because there are no curved sides, light interactions and light defraction from the glass of the lumen are minimized.

It should be mentioned at this point of the description that it is preferred to use disposable elements e.g. plastic, for the tubes and other components of the system through which blood fluids pass. In the preferred embodiment of the invention, lumen 22 is plastic but includes a pair of opposed optically transparent glass windows 38 between the source and detector. Of course, the reason for using disposable components is to eliminate the time-consuming and costly procedure of sterilization between uses of the system 10. The removable cover for housing 30 permits rapid coupling of the replaceable components to the more expensive electronic components and in the illustrated embodiment locator lugs 36 on the exterior of the lumen engage mating receptacles 37 within the housing to insure precise alignment.

The light source employed for the preferred embodiment of the invention is an infra-red emitting diode whose maximum output is at about 800 nm. The detector is a silicon photo transistor whose spectral sensitivity is also maximum near 800 nm so that the emitter and detector are matched for optimal spectral characteristics. A preferred receptor is the G.E. model L14G3 sensor. At a wavelength of 800 nm oxyhemoglobin ($HbO_2$) and reduced hemoglobin (HHb) transmit light equally so that transmission of light at this wave-length will only be affected by the total amount of hemoglobin in the blood and will be independent of the proportion of oxy-hemoglobin and reduced hemoglobin present. In other words, the system will be independent of blood oxygen saturation.

Figure 3:
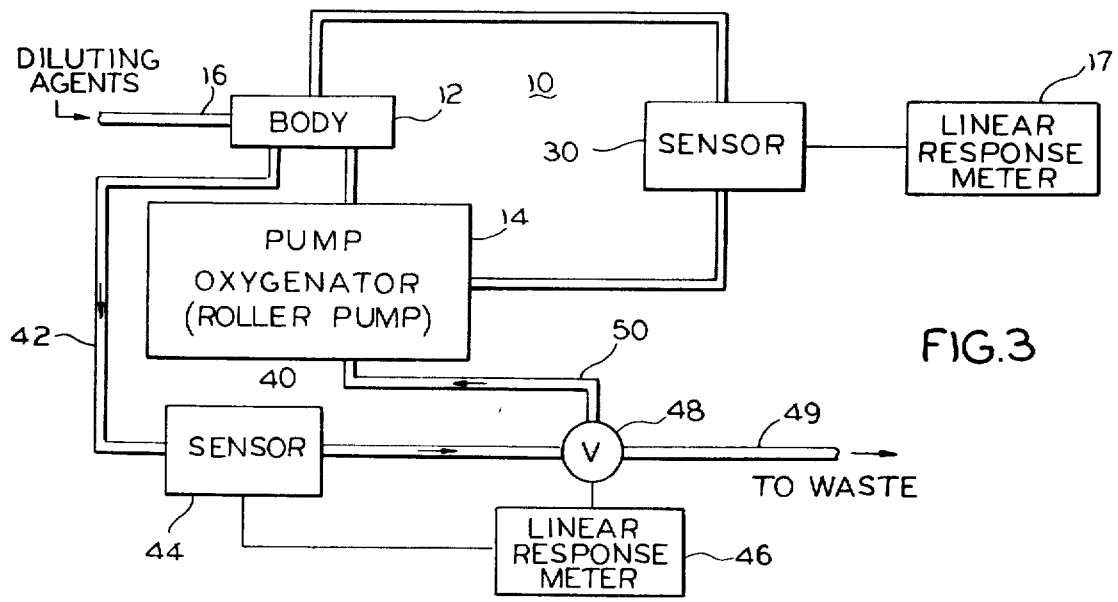
FIG. 3 is a schematic diagram of a combined monitor and blood suction line monitor and control system according to the present invention.

Referring next to FIG. 3, a more extensive use of the present invention is illustrated. This embodiment includes the monitor system 10 but also includes a blood suction line monitor and control system 40. By way of background, it should be mentioned that during typical open heart surgery, a large amount of blood may flow into the chest cavity, and it is common to recover this blood through a suction return line and pass it back to the oxygenator pump 14. Blood hematocrit levels in the suction return system are also important and it is desirable to maintain a careful watch on the level during the operative procedure. It also frequently happens that the levels are undesirably low such that the suction return should not be reintroduced to the body but should be diverted to waste. It would be highly desirable to provide a system which accomplishes those objectives automatically.

To this end, system 40 includes a blood system return line 42 (the suction creating means not being shown but being known to the art). A second blood hematocrit sensor 44 is coupled to line 42. Sensor 44 is the same as the sensor 30 illustrated in FIG. 2 and a linear response meter 46 is coupled to sensor 44 in the same manner as was illustrated for system 10 whereby the surgical team is provided with a visual indication of the blood hematocrit level being returned to the body from the patient's chest cavity. In addition, however, system 40 includes a provision for diverting the suction line blood flow to a waste receptacle in the event the levels are undesirably low.

This feature of the invention is made possible by the inclusion of a three-way solenoid valve 48 immediately downstream of sensor 40, one leg of valve 48 being coupled to the pump 14 for recirculating the suction return while a second leg of valve 48 is coupled to a waste disposal line 49 which in turn is coupled to a suitable receptacle (not shown). The circuitry for accomplishing this feature will be illustrated in FIG. 5.

Figure 4:
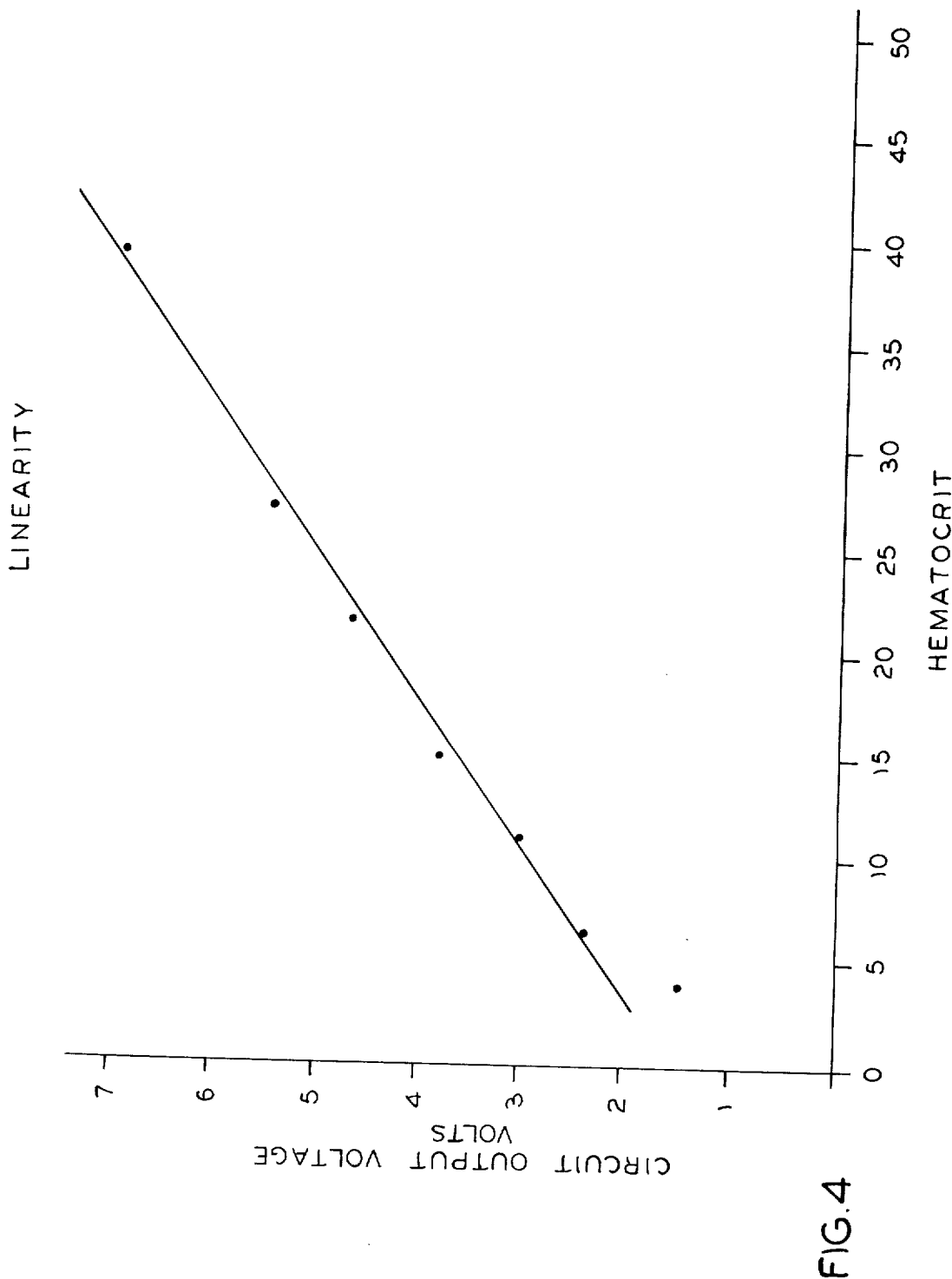
FIG. 4 is a linearity diagram.

Before proceeding with the description of circuitry, applicant wants to briefly refer to the linearity diagram included as FIG. 4. In that FIGURE the circuit output voltage from the photodetector 26 is plotted against hematocrit level using the equipment shown in FIG. 2. It will be appreciated then that a linear response may be built into the electrical components of the device.

Figure 5:
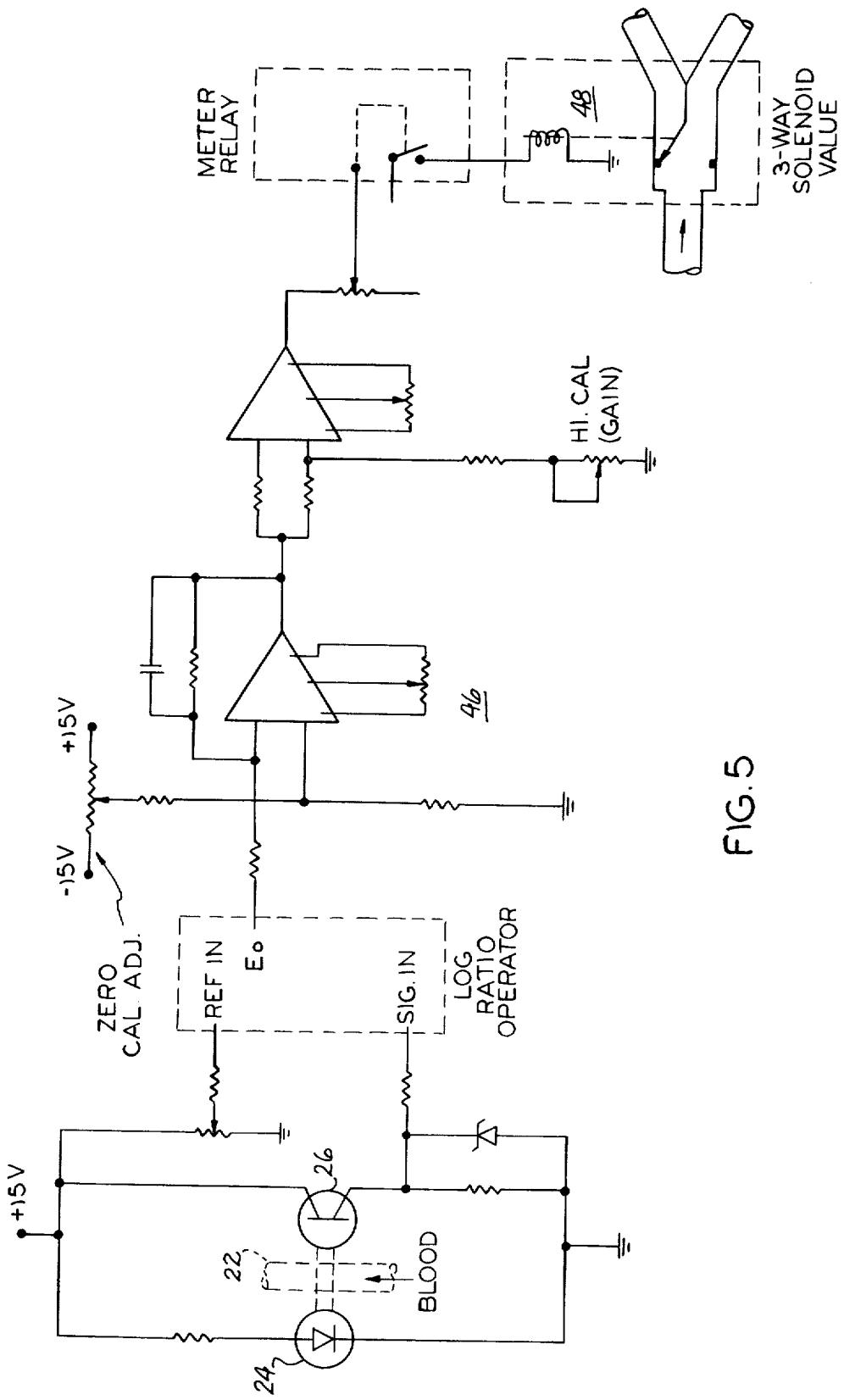
FIG. 5 is a wiring schematic of the electrical system useful for the monitor and control system of FIG. 4.

Finally, the wiring schematic for the preferred embodiment of the present invention is illustrated in schematic form in FIG. 5, the schematic including not only the system for providing a linearized input to the meter relay used in sensors 30 and 44, but also including the circuitry for activating the three-way solenoid valve 48. It should be understood that the circuitry illustrated is for that purpose alone and the invention is not to be limited thereby because it is expected that other suitable circuitry could be devised once the major features of the present invention have been read and understood.

The circuit is designed to amplify the signal generated by photosensor 26 so that a signal output voltage is obtained which is compatible with analog or digital meters for providing a direct readout. Preferably the control unit operates from standard line voltage which supplies electrical DC power to the sensor and amplifies the signal for proper voltage.

The current received at the photo-transducer detector is inversely proportional to the transmission characteristics of the intervening medium according to $I/I_o = -KCL$, where L is the length of the optical path, K is a constant, C is the concentration of the medium, I is the intersity of the transmitted light and Io is the intensity of the incident light.

The present invention can also be adapted for the monitor and control of other blood constituents. For such other uses, the light source and detector would have to be modified for output and sensitivity corresponding to the transmission characteristics of the fluid constituent to be monitored. So while the present invention has been disclosed in connection with two illustrated embodiments, it is not to be so limited but is to be limited solely by the claims which follow.

I claim:

1. A system for monitoring and controlling the level of blood hematocrit comprising:

an infra-red light source means;

an infra-red sensitive photo-transistor detector means opposing said light source means, said detector means being selected so as to produce a change in voltage dependent upon the amount of light impinging thereupon and having a spectral sensitivity at the wavelength of the light source means;

lumen means intermediate said light source means and said detector means, said lumen means being substantially optically transparent to the light emitted by said light source means; and meter means responsive to the voltage emitted from said detector means for indicating the quantity of hematocrit within a moving column of blood when said column is passed through said lumen means;

a three-way valve means downstream of said detector means and said light source means, said valve means being coupled to said lumen means, a first outlet of said valve means and a second outlet from said valve means; and means within said meter means for causing blood to flow from said lumen means to said first outlet when the blood hematocrit level is above a preselected value and to flow from said lumen to said second outlet when the blood hematocrit level is below said preselected value.

2. The device set forth in claim 1 wherein the maximum spectral output of the light source means and the maximum sensitivity of said detector are at approximately the same wavelength.

3. The device set forth in claim 2 wherein said wavelength is approximately 800 nm.

4. The device set forth in claim 1 wherein said light source means, detector means and lumen means are contained within a sensor housing adapted for preventing extraneous light from reaching the area between said light source means and detector means.

5. The device set forth in claim 1 wherein said housing means is interiorly coated with a non-reflective coating 6. The invention set forth in claim 1 wherein said lumen means is contructed of plastic and includes optically transparent glass windows at the area of said lumen means disposed between said light source means and said detector means.

7. The invention set forth in claim 1 wherein said meter means is a linear response meter.

8. The invention set forth in claim 1 wherein said valve means is a solenoid valve.

9. A device for monitoring the level of blood hematocrit in a moving blood column comprising:

a lumen for containing said column of blood, at least a portion of said lumen being optically transparent to light passing therethrough at a wavelength of approximately 800 nm;

a light source disposed adjacent said portion of said lumen for directing light having a wavelength of approximately 800 nm through said lumen;

a photo-transistor detector disposed on the opposite side of said portion of said lumen for receiving light from said light source and having a maximum spectral sensitivity at approximately 800 nm;

meter means coupled to said detector for indicating the quantity of hematocrit within said lumen;

a three-way valve means downstream of said detector means and said light source means coupled to said lumen means, a first outlet of said valve means and a second outlet from said valve means; and means within said meter means for causing blood to flow from said lumen to said first outlet when the blood hematocrit level is above a preselected value and to flow from said lumen to said second outlet when the blood hematocrit is below said preselected value.

10. A device for monitoring the level of blood hematocrit in a moving column of blood comprising:

an infra-red light source means;

an infra-red sensitive photo-transistor detector means opposing said light source means, said detector being selected so as to produce a change in voltage dependent upon the amount of light impinging thereupon and having a spectral sensitivity at the wavelength of the light source means;

housing means containing said light source and detector means;

tube means for conveying blood to said housing and away therefrom;

lumen means within said housing and disposed intermediate said light source and detector means, said lumen means being coupled at each end to said tube means and having a pair of parallel optically transparent window means at the portion of said lumen means intermediate said light source and detector means;

locating means on the exterior of said lumen means and means within said housing for engaging said locating means whereby said lumen means is located within said housing means only in a position where the light emitted from said light source is directed perpendicularly through said window means toward said detector means; and meter means coupled to said detector means and being responsive to the voltage emitted from said detector means for indicating the quantity of hematocrit within a moving column of blood when said column is passed through said lumen means.

11. The device set forth in claim 10 wherein said locating means comprises a plurality of lugs located on the exterior surface of said lumen means and adapted for engaging mating receptacles within said housing means.

* * * * *